(12) United States Patent
Koelker et al.

(10) Patent No.: US 12,390,134 B2
(45) Date of Patent: Aug. 19, 2025

(54) METHOD OF MANUFACTURING A SENSOR FOR DETECTING AN ANALYTE IN A BODY FLUID

(71) Applicant: Roche Diabetes Care, Inc., Indianapolis, IN (US)

(72) Inventors: Karl-Heinz Koelker, Mannheim (DE); Thilo Reschke, Mannheim (DE); Sebastian Kuebler, Mannheim (DE); David Kaspar Siebel, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1180 days.

(21) Appl. No.: 16/868,331

(22) Filed: May 6, 2020

(65) Prior Publication Data

US 2020/0261006 A1    Aug. 20, 2020

Related U.S. Application Data

(63) Continuation of application No. PCT/EP2018/080570, filed on Nov. 8, 2018.

(30) Foreign Application Priority Data

Nov. 8, 2017   (EP) .................................. 17200660

(51) Int. Cl.
*A61B 5/1473*   (2006.01)
*A61B 5/145*    (2006.01)
*A61B 5/1486*   (2006.01)

(52) U.S. Cl.
CPC ...... *A61B 5/14735* (2013.01); *A61B 5/14532* (2013.01); *A61B 5/14546* (2013.01); *A61B 5/14865* (2013.01); *A61B 2562/125* (2013.01)

(58) Field of Classification Search
CPC .......... A61B 2562/125; A61B 5/14532; A61B 5/14546; A61B 5/14735
See application file for complete search history.

(56) References Cited

U.S. PATENT DOCUMENTS 5,776,324 A    7/1998  Usala
6,001,239 A *  12/1999 Douglas ................... C12Q 1/26
                                                 205/793

(Continued)

FOREIGN PATENT DOCUMENTS

CN    1531650 A     9/2004
CN    103687535 A   3/2014

(Continued)

OTHER PUBLICATIONS

Kudryashov A. P., Biosensor Devices: Lectures, Minsk. BGU, 2003, 113 pages, cf. pp. 17-18.

(Continued)

*Primary Examiner* — Minh N Trinh
(74) *Attorney, Agent, or Firm* — Bose Mckinney & Evans LLP (57) ABSTRACT

A method for manufacturing a sensor for detecting an analyte in a body fluid is disclosed. In the inventive method a membrane layer is provided, and at least one first electrically conductive material is directly or indirectly deposited onto the membrane layer. At least one electrically insulating material is directly or indirectly deposited onto the at least one membrane layer and the at least one first electrically conductive material, and at least one second electrically conductive material is deposited directly or indirectly onto the electrically insulating material. An associated sensor is also disclosed.

6 Claims, 2 Drawing Sheets

(56) References Cited

U.S. PATENT DOCUMENTS

| | | | |
|---|---|---|---|
| 6,582,573 B2* | 6/2003 | Douglas | C12Q 1/001 204/403.11 |
| 7,003,336 B2 | 2/2006 | Holker et al. | |
| 12,004,858 B2* | 6/2024 | Oja | A61B 5/14503 |
| 2004/0140209 A1 | 7/2004 | Choi et al. | |
| 2005/0008537 A1 | 1/2005 | Mosoiu et al. | |
| 2006/0076236 A1 | 4/2006 | Shah et al. | |
| 2007/0173711 A1 | 7/2007 | Shah et al. | |
| 2009/0156920 A1 | 6/2009 | Kotzan et al. | |
| 2012/0088993 A1 | 4/2012 | Buck et al. | |
| 2012/0296186 A1* | 11/2012 | Ouyang | A61B 5/14532 600/347 |
| 2012/0323098 A1* | 12/2012 | Moein | A61B 5/14532 29/832 |
| 2014/0094671 A1 | 4/2014 | Boock et al. | |
| 2015/0005601 A1* | 1/2015 | Hoss | A61B 5/1473 600/345 |
| 2015/0241378 A1 | 8/2015 | Liu et al. | |
| 2015/0374270 A1 | 12/2015 | Shults et al. | |
| 2020/0261006 A1* | 8/2020 | Koelker | A61B 5/14735 |

FOREIGN PATENT DOCUMENTS

| | | | |
|---|---|---|---|
| EP | 1 797 817 A1 | 6/2007 | |
| JP | H09-182738 A | 7/1997 | |
| JP | H11-513914 A | 11/1999 | |
| JP | 2004-527769 A | 9/2004 | |
| JP | 2005-083994 A | 3/2005 | |
| JP | 2007-524816 A | 8/2007 | |
| JP | 2009-509166 A | 3/2009 | |
| JP | 2013-543405 A | 12/2013 | |
| JP | 2015-534483 A | 12/2015 | |
| RU | 2 622 087 C2 | 6/2017 | |
| RU | 2 707 819 C2 | 11/2019 | |
| WO | WO 2005/078424 A1 | 8/2005 | |
| WO | WO 2007/037970 A1 | 4/2007 | |
| WO | WO 2007/071562 A1 | 6/2007 | |
| WO | WO 2018/185171 A1 | 10/2018 | |

OTHER PUBLICATIONS

Zhebentyaev A. I., et al., Electrochemical Analysis Methods, Vitebsk, 2015, 106 pages, cf. pp. 6-7.

Chuyeshov, Promyšlennaya tekhnologiya lekarstv (Industrial technology of medications), V. 1, Kharkov, ed. NFAU (National Pharmaceutical University), 2002, p. 24, paragraphs 1, 2.

International Search Report and Written Opinion of the International Searching Authority, PCT/EP2018/080570, Jan. 28, 2019, 8 pages.

Hönes et al., Diabetes Technology and Therapeutics, vol. 10, Supplement 1, 2008, pp. 10-26.

* cited by examiner

METHOD OF MANUFACTURING A SENSOR FOR DETECTING AN ANALYTE IN A BODY FLUID

RELATED APPLICATIONS

This application is a continuation of PCT/EP2018/080570, filed Nov. 8, 2018, which claims priority to EP 17 200 660.3, filed Nov. 8, 2017, both of which are hereby incorporated herein by reference.

BACKGROUND

This disclosure generally relates to a sensor for detecting an analyte in a body fluid and a method for manufacturing thereof. The devices and methods according to this disclosure may mainly be used for continuous monitoring or long-term monitoring of an analyte concentration in a body fluid, such as for continuous or long-term monitoring of a glucose level or of the concentration of one or more other types of analytes in a body fluid. This disclosure may both be applied in the field of home care and in the field of professional care, such as in hospitals. Other applications are feasible.

Monitoring certain body functions, more particularly monitoring one or more concentrations of at least one metabolite concentration in a body fluid plays an important role in the prevention and treatment of various diseases. Such metabolites can include by way of ex-ample, but not exclusively, blood glucose, lactate, cholesterol or other types of analytes and metabolites. Without restricting further possible applications, the disclosure will be provided in the following text with reference to blood-glucose monitoring. However, additionally or alternatively, this disclosure can also be applied to other types of analytes, such as the analytes mentioned above.

In the field of continuous or long-term monitoring, the setup and the manufacturing of the sensors is a technical challenge. Typically, electrochemical sensors are used which transcutaneously are inserted into the body tissue of the user. The sensors typically comprise an elongated flexible substrate onto which a plurality of electrodes, including one or more working electrodes and one or more further electrodes such as one or more counter electrodes and/or one or more reference electrodes are applied.

U.S. Pat. No. 7,003,336 B2 discloses a sensor and method of making the same for implantation in a body. The sensor includes a substrate with notches cut in the substrate to form a necked down region in the substrate. The sensor further comprises at least one electrode formed from one or more conductive layers. Preferably, the thickness of the substrate ranges from approximately 25 µm to 350 µm, and the thickness of the substrate can range from 5 µm to 750 µm. The sensor may be incorporated into a sensor assembly which includes a needle having a slot. The notches creating the necked down region allow the substrate to slide into the slotted needle, which has the slot narrow enough to permit passage of the necked down region. A non-necked down region of the substrate is prevented from pulling out of the slotted needle through the slot. The slot of the slotted needle may also permit the necked down region of the substrate to slide down the slot.

WO 2007/071562 A1 discloses an implantable sensor that can be used for determining a concentration of at least one analyte in a medium, especially a body tissue and/or a body fluid. Said implantable sensor has a layered structure encompassing at least one insulating supporting substrate and at least two electrodes which are disposed in at least two different layer levels of the implantable sensor and are electrically separated from each other by means of the at least one insulating supporting substrate. The electrodes are provided with electrode surfaces which face the medium when the sensor is implanted and are in contact with the medium across large areas and in a substantially uniform manner either directly or via an analyte-permeable membrane layer.

WO 2005/078424 A1 discloses an analyte sensor for use in connection with a biofluid. The analyte sensor may comprise any suitable interface between the biofluid and a derivative of the biofluid and any suitable transducer of information concerning an analyte. At least one catalytic agent is provided in a locale or vicinity of the interface. The catalytic agent, such as a proteinaceous agent or a non-proteinaceous, organic-metal agent, is sufficient to catalyze the degradation of reactive oxygen and/or nitrogen species that may be present in the vicinity of the interface. An analyte-sensing kit and a method of sensing an analyte are also described.

Despite the advantages of these known sensors for transcutaneous insertion, a large number of technical challenges remain. Several of these challenges are related to the use of a carrier substrate which has to be functionalized by using several process steps. Conductive leads have to be applied to the insulating substrate with high precision and low tolerances, requiring costly manufacturing techniques and materials. Further, the process of manufacturing generally requires a high number of process steps, including manufacturing of the substrate, wet-chemical processing of coatings, drying and verification or inspection steps. As mentioned, most of these process steps require a very high precision, due to the fact that the chain of tolerances is very tight. Further, influences of heat and other manufacturing conditions have to be considered, such as drying conditions, which may lead to distortions of the substrate. High costs for materials and inspection have to be taken into account, mainly due to the fact that cutting-edge manufacturing processes are involved. The use of auxiliary materials, which per se are not required for the actual measurement may additionally raise the costs of manufacturing. Further, the use of certain materials in the substrate setup may have an impact on the measurement, such as electrochemically active metals like Cu. Consequently, in order to guarantee the biocompatibility of the analyte sensor, the substrate or the sensor typically have to be sealed against bodily fluids.

SUMMARY

This disclosure teaches a sensor for detecting an analyte in a body fluid and a method for manufacturing the sensor which address the above-mentioned technical challenges. The sensor disclosed herein can be manufactured at low cost, using a process having a low number of process steps.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "membrane layer," "electrically conductive material," and "electrically insulating material," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect, a method for manufacturing a sensor for detecting an analyte in a body fluid is disclosed. The sensor specifically may be or may comprise an analyte sensor configured for at least partial implantation, specifically transcutaneous insertion, into a body tissue of a user, more specifically an analyte sensor for continuous monitoring of the analyte. The method comprises the following steps which specifically may be performed in the given order or in a different order, such as in a reverse order. Thus, a different order may also be possible. Further, two or more process steps may be performed simultaneously or partially simultaneously. Further, one or more than one or even all of the method steps may be performed once or more than once or even repeatedly or continuously. The method may further comprise additional method steps which are not listed. The method comprises the following steps:
  a) providing a membrane layer;
  b) depositing at least one first electrically conductive material directly or indirectly onto the membrane layer;
  c) depositing at least one electrically insulating material directly or indirectly onto the at least one membrane layer and the at least one first electrically conductive material; and
  d) depositing at least one second electrically conductive material directly or indirectly onto the electrically insulating material.

The process steps, as outlined above, may be performed in the given order or, as an example, in a reverse order. In the given order, the membrane layer may function as a carrier, onto which, in steps b)-d), a deposition takes place. In a reverse order, an additional carrier may be provided, the at least one second electrically conductive material may directly or indirectly be deposited thereon, followed by the depositing of the electrically insulating material, followed by the depositing of the at least one first conductive material and, subsequently, by adding the membrane layer on top. Thereafter, the carrier may be removed from the setup, e.g., by peeling off the carrier, thereby obtaining the same or a similar setup as in the given order as listed above.

The step of providing the membrane layer may comprise providing a membrane layer or a part thereof which are already ready established and/or readily manufactured such as a commercially manufactured membrane layer or a membrane layer manufactured in a separate step or process. Additionally or alternatively, the step of providing the membrane layer may also comprise fully or partially manufacturing the at least one membrane layer or a part thereof, such as by manufacturing from a liquid phase, printing or the like.

As will be outlined in further detail below, the method may further comprise applying at least one test chemical, wherein the test chemical is applied such that the test chemical is in physical contact with the at least one first electrically conductive material. The application of the at least one test chemical, which, as an example, may comprise at least one chemical reagent, may take place, e.g., in step b) and/or in a separate method step. The at least one test chemical may be in contact with a part of the first electrically conductive material, which may be or may define a working electrode.

The term "test chemical" as used herein is a broad term and is to be given its ordinary and customary meaning to a person of ordinary skill in the art and is not to be limited to a special or customized meaning. The term specifically may refer, without limitation, to at least one material or mixture of materials, such as to at least one chemical compound or at least one mixture of chemical compounds, which are suited to perform at least one detection reaction for qualitatively and/or quantitatively detecting the at least one analyte. Specifically, the at least one test chemical may comprise at least one chemical reagent, such as at least one enzyme, which is suited for performing at least one detectable reaction in the presence of the at least one analyte. As an example, the reaction may be an enzymatic redox reaction. Other reactions are possible. The at least one test chemical may comprise one or more additional materials, such as one or more electrically conductive materials and/or materials which are suited for improving a charge carrier transfer such as an electron transfer. As an example for possible test chemicals, reference may be made, e.g., to J. Hönes et al.: The Technology Behind Glucose Meters: Test Strips, Diabetes Technology & Therapeutics, Vol. 10, Supplement 1, 2008 and the test chemicals and chemical reagents listed therein. It shall be noted, however, that other test chemicals are feasible.

The term "sensor" as used herein is a broad term and is to be given its ordinary and customary meaning to a person of ordinary skill in the art and is not to be limited to a special or customized meaning. The term specifically may refer, without limitation, to an arbitrary element or device configured for detecting at least one condition or for measuring at least one measurement variable. The sensor specifically may be or may comprise an analyte sensor for at least partial implantation into a body tissue of a user, more specifically an analyte sensor for continuous monitoring of the analyte. The sensor specifically may be a monolithic sensor element.

Further, the term "analyte" as used herein is a broad term and is to be given its ordinary and customary meaning to a person of ordinary skill in the art and is not to be limited to a special or customized meaning. The term specifically may refer, without limitation, to an arbitrary element, component or compound which may be present in a body fluid and the concentration of which may be of interest for, e.g., a user or a healthcare professional. Specifically, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be used and/or any combination of analytes may be determined.

The term "user" as used herein is a broad term and is to be given its ordinary and customary meaning to a person of ordinary skill in the art and is not to be limited to a special or customized meaning. The term specifically may refer, without limitation, to a human being or an animal, independent from the fact that the human being or animal, respectively, may be in a healthy condition or may suffer from one or more diseases. As an example, the user may be a human being or an animal suffering from diabetes. However, additionally or alternatively, this disclosure may be applied to other types of users.

Generally, an arbitrary type of body fluid may be used. Preferably, the body fluid is a body fluid which is present in a body tissue of the user, such as in the interstitial tissue. Thus, as an example, the body fluid may be selected from the group consisting of blood and interstitial fluid. However, additionally or alternatively, one or more other types of body fluids may be used. The body fluid generally may be contained in a body tissue. Thus, generally, the detection of the at least one analyte in the body fluid may preferably be determined in vivo.

The sensor may fully or partially be implanted into the body tissue, specifically transcutaneously. The sensor specifically may have a length of no more than 50 mm, e.g., a length of 2 mm to 30 mm. The sensor further may have a width of no more than 5 mm, e.g., a width of 0.1 mm to 2 mm. The sensor specifically may be a flexible sensor that is deformable under typical forces occurring in an implanted state. The sensor may have a thickness of no more than 2 mm, preferably a thickness of 0.2 to 1.0 mm. The sensor specifically may be strip-shaped, having the shape of a thin elongated strip. The sensor specifically may be biocompatible, e.g., by having a biocompatible coating.

The term "membrane layer," as used herein, is a broad term and is to be given its ordinary and customary meaning to a person of ordinary skill in the art and is not to be limited to a special or customized meaning. The term specifically may refer, without limitation, to a layer of at least one material, which provides a selective barrier. Thus, the membrane layer generally may selectively allow for one or more molecules and/or compounds to pass, whereas other molecules and/or compounds are stopped by the membrane layer. In the methods and devices as proposed, specifically using a reversed setup as compared to conventional methods and devices using a setup on a substrate, the membrane layer specifically may also function as a substrate. Consequently, the membrane layer specifically may provide mechanical stability. Thus, the membrane layer, as an example, may be strip-shaped, e.g., having the shape of an elongated strip having the length and width of the sensor as discussed above. The membrane layer, as an example, may have a thickness sufficient for providing mechanical stability. Examples of potential materials for the membrane layer and for potential thicknesses of the membrane layer will be given below.

The providing of the membrane layer may take place by using several techniques and methods. Thus, as an example, the providing may simply take place by introducing a ready-to-use membrane layer into the process. As an example, the membrane layer may be provided as an endless sheet or strip, e.g., in a reel-to-reel process, and the providing of the membrane layer for the sensor may involve a cutting process, by cutting. A plurality of sensors may be manufactured on the endless sheet or strip. Additionally or alternatively, the providing of the membrane layer may also take place by fully or partially manufacturing the membrane layer, e.g., by coating, casting, printing or in situ polymerization. Thus, as an example, the membrane layer may be manufactured by casting an appropriate liquid into a mold, e.g., a mold having the shape of the sensor or a plurality of sensors, e.g., followed by a sintering process or a polymerization process. Again, additionally or alternatively, the membrane layer for one or more sensors may be printed or coated onto a transfer substrate. Combinations of such techniques are feasible.

The term "electrically conductive material," as used herein, is a broad term and is to be given its ordinary and customary meaning to a person of ordinary skill in the art and is not to be limited to a special or customized meaning. The term specifically may refer, without limitation, to a material which is capable of sustaining an electrical current. Specifically, the electrically conductive material may be or may comprise at least one metal, such as one or more of gold, copper, silver, palladium or platinum. Additionally or alternatively, the at least one electrically conductive material may be or may comprise at least one electrically conductive compound, such as at least one electrically conductive organic or inorganic compound. As an example, compounds such as Ag/AgCl may be mentioned. Additionally or alternatively, the at least one electrically conductive material may be or may comprise at least one nonmetallic electrically conductive material, e.g., carbon paste.

As will be outlined in further detail below, the at least one first electrically conductive material may be deposited directly or indirectly onto the membrane layer. Thus, there may be a direct physical contact between the electrically conductive material and the membrane layer, or at least one additional material may be deposited on the membrane layer before depositing the first electrically conductive material. Thus, as an example, in the region of a working electrode, a test chemical, such as a test chemical containing at least one chemical reagent, may be deposited onto the membrane layer before depositing the first electrically conductive material onto the test chemical and, thus, indirectly onto the membrane layer. In other regions, the first electrically conductive material may be in direct contact with the membrane layer, e.g., in one or more regions in which electrode pads are formed which directly and without additional material form an electrode in contact with the membrane layer. Generally, the at least one first electrically conductive material may be in contact with at least one test chemical, such as with at least one test chemical containing at least one chemical reagent.

The at least one first electrically conductive material specifically may comprise one or more electrically conductive layers deposited in a patterned fashion. Thus, as an example, the depositing of the at least one first electrically conductive material may imply a patterned deposition of the one or more electrically conductive layers, e.g., by using printing techniques such as screen printing and/or stencil printing. Again, additionally or alternatively, a large area deposition may take place, followed by a subsequent patterning step, e.g., by laser patterning or etching. By depositing the at least one first electrically conductive material in a patterned fashion, one or more electrode pads may be deposited directly or indirectly onto the membrane layer, e.g., one or more round, oval or polygonal electrode pads, e.g., for one or more of at least one working electrode or at least one further electrode, e.g., at least one of a counter electrode or a reference electrode. Additionally, by depositing the at least one first electrically conductive material directly or indirectly onto the membrane layer, one or more electrically conductive leads for electrically contacting at least one electrode may be deposited, e.g., one or more electrically conductive leads connecting the one or more above-mentioned electrode pads with one or more contact pads. Thus, as an example, the sensor may have a contact portion at one end, and the electrically conductive leads may extend from one or more contact pads in the contact portion, along an axis of longitudinal extension of the sensor, to one or more electrode pads close to an opposing end of the sensor.

The terms "first" and "second" as well as further numerals used for identifying elements generally are meant to provide nomenclature, only. Thus, specifically, a "first" element may be present without a "second" or "third" element being present and vice versa, unless explicitly mentioned. Further, in case several elements are identified by identifying numerals, these identifying numerals not necessarily indicate that the elements are different. Thus, as an example, the at least one first electrically conductive material and the at least one second electrically conductive material may be chosen such that the second electrically conductive material is fully or partially different from the first electrically conductive material or alternatively, such that the second electrically conductive material is fully or partially chosen identical to the first electrically conductive material. Thus, as an example, one and the same metallic material may be chosen both in the first electrically conductive material and in the second electrically conductive material. Consequently, as an example, even though the first and second electrically conductive materials may form different structural elements such as different electrodes, the same materials may be used in these different structural elements.

The term "electrically insulating material," as used herein, is a broad term and is to be given its ordinary and customary meaning to a person of ordinary skill in the art and is not to be limited to a special or customized meaning. The term specifically may refer, without limitation, to a material or combination of materials which prevent the transfer of electrical charges and which do not sustain a significant electrical current. Specifically, without limiting other possibilities, the at least one electrically insulating material may be or may comprise at least one insulating resin, such as insulating epoxy resins used in manufacturing electronic printed circuit boards.

The depositing of the at least one electrically insulating material directly or indirectly onto the at least one membrane layer, again, may take place in a non-patterned and/or in a patterned fashion. Specifically, the at least one electrically insulating material may be deposited by using at least one liquid phase processing step, depositing the at least one electrically insulating material as a liquid, e.g., followed by a setting process and/or an in situ polymerization or curing process. Thus, as an example, coating or printing techniques may be used, specifically for depositing one or more resins. Again, printing techniques such as screen printing or stencil printing are possible. Further, dosing techniques such as using one or more dosing needles, are feasible. Other deposition techniques may be used in addition or alternatively. The at least one electrically insulating layer, as an example, may have a thickness of <800 µm, preferred <500 µm, further preferred <300 µm or <200 µm, such as a thickness of 1 µm to 250 µm, specifically 5 to 50 µm. As an example, the electrically insulating layer may have at least a thickness which is suitable to sustain the mechanical stress when implanted into the body tissue and, still, remains electrically insulating. The thickness, however, should be kept as low as possible, since obtaining homogeneous layers generally is more challenging for thick layers.

The at least one electrically insulating material specifically may be deposited in such a way that the at least one membrane layer and the at least one first electrically conductive material are fully covered with the at least one electrically insulating material. Thus, an electrical insulation barrier may be provided by the at least one electrically insulating material between the subsequent at least one second electrically conductive material on the one hand and the at least one first electrically conductive material and the membrane layer on the other hand. Thus, firstly, an electrical contact between the first electrically conductive material and the second electrically conductive material may be prevented by the electrically insulating material. Further, a contact between one or more analytes entering the sensor through the membrane layer and the second electrically conductive material may be prevented. Thus, the electrically insulating material which is deposited directly or indirectly onto the at least one membrane layer and the at least one first conductive material may take over the function of the insulating substrate in conventional sensors.

With respect to the second electrically conductive material, again, reference may be made to the definitions and possible material mentioned above in the context of the first electrically conductive material. Similar to the first electrically conductive material, the depositing of the at least one second electrically conductive material directly or indirectly onto the electrically insulating material specifically may take place in a patterned fashion. Thus, reference may be made to the techniques mentioned above in the context of the first electrically conductive material which also may be applied for depositing the second electrically conductive material. The depositing of the at least one second electrically conductive material specifically may take place in such a way that the at least one second electrically conductive material is in contact with the electrically insulating material, only, whereas a contact between the first electrically conductive material and the second electrically conductive material and/or a contact between the second electrically conductive material and the membrane layer is avoided. The second electrically conductive material specifically may be patterned in such a way that one or more electrode pads are generated, e.g., again, one or more of round, oval or polygonal electrode pads. Thus, as an example, the second electrically conductive material specifically may be patterned in such a way that one or more of at least one counter electrode or at least one reference electrode are generated. Further, again, additionally, by depositing the at least one second electrically conductive material in a patterned fashion, one or more electrically conductive leads for electrically contacting at least one electrode pad may be deposited, e.g., one or more electrically conductive leads connecting the one or more above-mentioned electrode pads with one or more contact pads. Thus, as an example, and as mentioned above, the sensor may have a contact portion at one end, and the electrically conductive leads may extend from one or more contact pads in the contact portion, along an axis of longitudinal extension of the sensor, to one or more electrode pads close to an opposing end of the sensor.

The method for manufacturing the sensor for detecting the at least one analyte, which specifically may be a sensor for continuous monitoring or long-term monitoring of the at least one analyte, may be embodied or further developed in various ways. Some of these options are outlined in the following and may be realized in an isolated fashion or in combination.

Thus, as outlined above, the membrane layer is permeable for the at least one analyte to be detected. Thus, as an example, the membrane layer may be permeable for one or more of blood glucose, lactate, cholesterol or other types of analytes.

The step of depositing the at least one first electrically conductive material, i.e., step b) in the above-mentioned sequence of steps, specifically may comprise forming at least one electrode pad of a working electrode. As outlined above, the electrode pad, as an example, may have a round, oval or polygonal shape and may, as an example, be fully or partially made of at least one metal layer. Other possibilities are given.

For the working electrode, specifically, the use of one or more test chemicals may be envisaged. Thus, the method may further comprise depositing at least one test chemical onto the membrane layer before or simultaneously to step b), wherein the test chemical is configured for performing at least one detection reaction in the presence of the analyte to be detected. Test chemicals which may be used herein are generally known to the skilled person. Thus, as an example, the at least one test chemical may be or may comprise at least one enzyme configured for performing a reaction in the presence of the at least one analyte. Further components may be present, such as one or more electrochemical mediators or the like. For potential embodiments, reference may also be made to the above-mentioned related art documents, such as to J. Hönes et al.: The Technology Behind Glucose Meters: Test Strips, Diabetes Technology & Therapeutics, Vol. 10, Supplement 1, 2008. The test chemical specifically may be deposited in a patterned fashion. Thus, as an example, one or more test chemical pads may be deposited directly or indirectly onto the membrane, followed by depositing the at least one electrode pad for the working electrode onto the one or more test chemical pads. The one or more working electrode pads specifically may be dimensioned and positioned such that they are in contact with the test chemical, only, whereas a direct contact with the membrane layer may be avoided. It shall be noted, however, that other options are feasible.

In addition to the at least one working electrode pad or as an alternative, step b) may also comprise forming at least one electrode pad for at least one further electrode. As outlined above, the at least one further electrode specifically may be selected from the group consisting of a counter electrode and a reference electrode. Thus, as an example, at least one working electrode pad and, additionally, at least one of at least one counter electrode pad or at least one reference electrode pad may be deposited directly or indirectly onto the membrane. The at least one further electrode pad specifically may at least partially be formed of at least one redox material, specifically of Ag/AgCl.

As mentioned above, step b) may also comprise forming one or more electrically conductive leads for contacting the at least one working electrode and/or the at least one further electrode. Thus, step b) may also comprise forming at least one electrically conductive lead for electrically contacting at least one electrode, specifically at least one electrode selected from the group consisting of a working electrode and at least one further electrode, more specifically at least one of a counter electrode and a reference electrode.

In case one or more electrically conductive leads are provided in step b), these electrically conductive leads, as an example, may be separated from the membrane layer, e.g., in order to avoid a direct contact between one or more analytes entering the sensor through the membrane and the first electrically conductive material of the electrically conductive leads. In order to provide this separation, specifically, before forming the at least one conductive lead for electrically contacting the at least one electrode, the method may comprise depositing at least one electrically insulating layer onto the at least one membrane layer, wherein the at least one conductive lead is formed such that the electrically insulating layer is disposed in between the conductive lead and the membrane. Thereby, a full or partial separation between the electrically conductive lead and the membrane may be provided. For the at least one electrically insulating layer, having electrically insulating properties as defined above, as an example, the same materials as for the electrically insulating material in step c) may be used. The use of other types of materials, however, is possible too. The deposition of the at least one electrically insulating layer may, again, take place in a patterned fashion, such that the electrode pads for the working electrode and the at least one further electrode such as the counter electrode and/or the reference electrode still may be deposited onto the membrane, e.g., by depositing these electrode pads onto regions of the membrane which are not covered by the electrically insulating layer. Thus, again, liquid deposition techniques may be used for producing the electrically insulating layer, e.g., printing techniques such as screen printing or stencil printing. Again, as for the electrically insulating material in step c), the electrically insulating layer, as an example, may fully or partially be made of a resin, e.g., an epoxy resin, e.g., a resin as typically used for circuit board manufacturing.

As outlined above, in the step of depositing the at least one second electrically conductive material, i.e., step d) in the above-mentioned list of process steps, specifically one or more of at least one electrode pad, at least one electrically conductive lead or at least one contact pad may be formed. Thus, step d) may comprise forming at least one electrode pad for at least one back electrode selected from the group consisting of a counter electrode and a reference electrode. As used herein, the term "back electrode" generally refers to an electrode fully or partially formed within the second electrically conductive layer, on a side of the electrically conductive material opposing the first electrically conductive material. Step d) may further comprise forming at least one conductive lead for electrically contacting the at least one back electrode. The at least one back electrode specifically may comprise at least one electrically conductive redox material, specifically Ag/AgCl.

The at least one working electrode and, optionally, the at least one further electrode may form one or more front electrodes which, preferably, are deposited directly onto the membrane layer. The at least one front electrode and the at least one back electrode may be deposited on opposing sides of the at least one electrically insulating material. As discussed above, contact pads may be provided for electrically contacting the at least one front electrode and the at least one back electrode, respectively. Thus, at least one front electrode contact pad may be provided, which may be electrically connected to the at least one front electrode via at least one electrically conductive front electrode lead. Further, at least one electrically conductive back electrode lead may be provided, for connecting the at least one back electrode contact pad with the at least one back electrode. The contact pads, i.e., the at least one front electrode contact pad and the at least one back electrode contact pad, both may be electrically contactable from one and the same side of the sensor. Thus, as an example, the contact pads, both for the at least one front electrode and for the at least one back electrode, may remain uncovered by insulating material and may be located on a back side of the sensor, opposing the membrane layer. Consequently, both the front electrode and the back electrode may be contacted from one and the same side, which provides advantages in the electrical connecting technology when the sensor is assembled into a sensor device for detecting the at least one analyte.

As outlined above, the electrically insulating material as used in step c) specifically may comprise at least one electrically insulating resin. As an example, one or more epoxy resins may be used. Other possibilities are given.

For the membrane layer, as outlined above, several materials may be used, standalone or in combination. Thus, as an example, the membrane layer specifically may comprise one or more of: a polyurethane; a hydrogel; a polyacrylate. These types of membranes are generally known in the art. As an example, hydrogel membranes may be used, e.g., membranes as disclosed in WO 2007/071562 A1 and/or in WO 2005/078424 A1. However, other types of sensor setups may be used. The membrane layer specifically may have a thickness of 1 µm to 150 µm.

As outlined above, the method comprises a plurality of deposition steps. Therein, specifically, a patterned deposition is feasible in various ways. For patterning, specifically, printing techniques are feasible. As an example, one or more of method steps a) to d) may make use of at least one printing method, such as screen printing or stencil printing. It shall be noted, however, that other patterned or non-patterned deposition techniques may be used alternatively or in addition.

In a further aspect of this disclosure, a sensor for detecting an analyte in a body fluid is disclosed. The sensor specifically may be made by using the methods according to any one of the embodiments disclosed above or disclosed in further detail below. Consequently, for definitions and optional embodiments, reference may be made to the description of the method. The sensor comprises the following elements which preferably are provided in the given order. Additional elements are feasible.

Thus, the sensor comprises:
i) at least one membrane layer;
ii) at least one first electrically conductive material directly or indirectly deposited on the membrane layer, wherein, specifically, at least one test chemical may be in contact with the at least one first electrically conductive material, specifically for forming at least one working electrode;
iii) at least one electrically insulating material directly or indirectly deposited on the at least one membrane layer and the at least one first conductive material; and
iv) at least one second electrically conductive material directly or indirectly deposited onto the electrically insulating material.

As outlined above, the sensor specifically may be obtainable or obtained by using the method according to any one of the preceding method claims.

Thus, as compared to conventional techniques in which a layer setup is deposited on both sides of an electrically insulating substrate which is not permeable for the analyte, the sensor according to this disclosure specifically may comprise a type of top-down or bottom-up setup depending on whether one starts with the membrane or the second conductive material in which the above-mentioned materials and layers are deposited onto the membrane which may be permeable for the analyte to be detected. This setup, in the final product, may be visible in a microscopic inspection of a cross-section of the layer setup, since, firstly, the sensor specifically may not comprise an insulating substrate which is not permeable for the analyte to be detected and since, further, the inverted deposition onto the membrane, as an example, is distinguishable from a setup in which the membrane is deposited onto the remaining layers.

For optional embodiments of the sensor, reference may widely be made to the method described above or described in further detail below. Thus, as an example, the first electrically conductive material may form at least part of at least one working electrode. The working electrode specifically may further comprise at least one test chemical deposited on the membrane and in between the membrane and the first electrically conductive material, wherein the test chemical is configured for performing at least one detection reaction in the presence of the analyte to be detected. The first electrically conductive material may form at least one working electrode pad in contact with the test chemical, for electrochemically detecting the detection reaction, e.g., by using conventional amperometric and/or potentiometric techniques.

The first electrically conductive material further may form at least part of at least one electrode selected from the group consisting of a counter electrode and a reference electrode. This at least one further electrode specifically may comprise at least one redox material, specifically Ag/AgCl.

The first electrically conductive material further may form at least one electrically conductive lead for electrically contacting at least one electrode formed within the first electrically conductive material, specifically at least one electrode selected from the group consisting of a working electrode and at least one further electrode, more specifically at least one of a counter electrode and a reference electrode.

As further outlined above, the sensor may further comprise at least one electrically insulating layer in between the membrane and the first electrically conductive material. Further, the second electrically conductive layer may comprise at least one back electrode selected from the group consisting of a counter electrode and a reference electrode. The second electrically conductive layer may further comprise at least one electrically conductive lead for electrically contacting the at least one back electrode.

For rendering the sensor biocompatible, one or more additional measures may be taken. Thus, as an example, the sensor may further comprise at least one biocompatibility layer fully or partially surrounding the sensor. This at least one compatibility layer, as an example, may comprise the same material as the at least one membrane layer and may avoid components of the sensor entering the body tissue. As an example, the at least one compatibility layer may comprise at least one polyacrylate material. The compatibility layer, as an example, may be made by dip coating the sensor into an appropriate liquid. Other techniques are feasible.

As outlined above, the sensor specifically may be made avoiding a substrate, specifically a substrate which is not permeable for the at least one analyte to be detected. Thus, specifically, the sensor, besides the membrane, may not comprise any substrate, specifically no substrate extending over the full width of the sensor.

The method and the sensor according to one or more of the embodiments given above or given in further detail below provide a large number of advantages over known methods and sensors. Thus, specifically, the substrate is typically used in manufacturing implantable sensors, such as a flexible circuit board substrate or a polyimide substrate, may be avoided and may be replaced by the membrane, which is a functional layer contributing to the functionality of the sensor. Consequently, the sensor function and the mechanical stability function of the substrate may be combined. Process steps which do not contribute to the functionality of the sensor may thereby be avoided. The costs for materials and for testing, which are typically involved in sensor manufacturing using a separate substrate, may thus be reduced. Further, the sensor setup may be made completely of elements which are required for the electrochemical measurement.

Further, the inverted setup, also referred to as a "top-down" setup, may significantly reduce the number of manufacturing steps. Thus, in typical and conventional sensor manufacturing, more than nine process steps are required, including substrate manufacturing, preparing the coating materials, drying and testing. By using a reduced number of process interfaces, further, tight tolerances may be achieved.

The manufacturing according to the process as proposed further allows for a large number of degrees of freedom for the geometry of the sensor. Thus, as outlined above, various techniques may be used for providing the membrane layer having an arbitrary shape. The use of highly flexible materials, specifically for the membrane layer, may further reduce mechanical limitations. Further, a high degree of miniaturization is possible, and the geometry of the overall sensor may be chosen arbitrarily and according to the specific requirements.

Summarizing and without excluding further possible embodiments, the following embodiments may be envisaged:

EMBODIMENT 1

A method for manufacturing a sensor for detecting an analyte in a body fluid, specifically an analyte sensor for at least partial implantation into a body tissue of a user, more specifically an analyte sensor for continuous monitoring of the analyte, the method comprising the following steps:

a) providing a membrane layer;

b) depositing at least one first electrically conductive material directly or indirectly onto the membrane layer;

c) depositing at least one electrically insulating material directly or indirectly onto the at least one membrane layer and the at least one first electrically conductive material; and d) depositing at least one second electrically conductive material directly or indirectly onto the electrically insulating material.

EMBODIMENT 2

The method according to the preceding embodiment, wherein the membrane layer is permeable for the analyte to be detected.

EMBODIMENT 3

The method according to any one of the preceding embodiments, wherein step b) comprises forming at least one electrode pad of a working electrode.

EMBODIMENT 4

The method according to the preceding embodiment, the method further comprising depositing at least one test chemical onto the membrane layer before or simultaneously to step b), wherein the test chemical is configured for performing at least one detection reaction in the presence of the analyte to be detected.

EMBODIMENT 5

The method according to the preceding embodiment, wherein the electrode pad of the working electrode is at least partially deposited onto the test chemical.

EMBODIMENT 6

The method according to any one of the preceding embodiments, wherein step b) comprises forming at least one electrode pad for at least one further electrode selected from the group consisting of a counter electrode and a reference electrode.

EMBODIMENT 7

The method according to the preceding embodiment, wherein the at least one electrode pad is at least partially formed of at least one redox material, specifically of Ag/AgCl.

EMBODIMENT 8

The method according to any one of the preceding embodiments, wherein step b) comprises forming at least one electrically conductive lead for electrically contacting at least one electrode, specifically at least one electrode selected from the group consisting of a working electrode and at least one further electrode, more specifically at least one of a counter electrode and a reference electrode.

EMBODIMENT 9

The method according to the preceding embodiment, wherein the method further comprises, before forming the at least one electrically conductive lead for electrically contacting the at least one electrode, depositing at least one electrically insulating layer onto the at least one membrane layer, wherein the at least one electrically conductive lead is formed such that the electrically insulating layer is disposed in between the conductive lead and the membrane layer.

EMBODIMENT 10

The method according to the preceding embodiment, wherein the at least one electrically insulating layer is at least partially formed by using at least one electrically insulating resin.

EMBODIMENT 11

The method according to any one of the preceding embodiments, wherein step d) comprises forming at least one electrode pad for at least one back electrode selected from the group consisting of a counter electrode and a reference electrode.

EMBODIMENT 12

The method according to the preceding embodiment, wherein step d) further comprises forming at least one electrically conductive lead for electrically contacting the at least one back electrode.

EMBODIMENT 13

The method according to any one of the two preceding embodiments, wherein the at least one back electrode comprises at least one electrically conductive redox material, specifically Ag/AgCl.

EMBODIMENT 14

The method according to any one of the preceding embodiments, wherein the electrically insulating material comprises at least one electrically insulating resin.

EMBODIMENT 15

The method according to any one of the preceding embodiments, wherein the membrane layer comprises one or more of: a polyurethane; a hydrogel; a polyacrylate.

EMBODIMENT 16

The method according to any one of the preceding embodiments, wherein the membrane layer has a thickness of 1 µm to 100 µm.

EMBODIMENT 17

The method according to any one of the preceding embodiments, wherein one or more of method steps a) to d) comprise using at least one printing method.

EMBODIMENT 18

A sensor for detecting an analyte in a body fluid, the sensor comprising:
  i) at least one membrane layer;
  ii) at least one first electrically conductive material directly or indirectly deposited on the membrane layer;
  iii) at least one electrically insulating material directly or indirectly deposited on the at least one membrane layer and the at least one first electrically conductive material; and
  iv) at least one second electrically conductive material directly or indirectly deposited onto the electrically insulating material.

EMBODIMENT 19

The sensor according to the preceding embodiment, wherein the sensor is obtainable or obtained by using the method according to any one of the preceding method claims.

EMBODIMENT 20

The sensor according to any one of the preceding embodiments referring to a sensor, wherein the first electrically conductive material forms at least part of at least one working electrode.

EMBODIMENT 21

The sensor according to the preceding embodiment, wherein the working electrode further comprises at least one test chemical deposited on the membrane and in between the membrane and the first electrically conductive material, wherein the test chemical is configured for performing at least one detection reaction in the presence of the analyte to be detected.

EMBODIMENT 22

The sensor according to any one of the preceding embodiments referring to a sensor, wherein the first electrically conductive material forms at least part of at least one further electrode selected from the group consisting of a counter electrode and a reference electrode.

EMBODIMENT 23

The sensor according to the preceding embodiment, wherein the at least one electrode comprises at least one redox material, specifically Ag/AgCl.

EMBODIMENT 24

The sensor according to any one of the preceding embodiments referring to a sensor, wherein the first electrically conductive material forms at least one electrically conductive lead for electrically contacting at least one electrode, specifically at least one electrode selected from the group consisting of a working electrode and at least one further electrode, more specifically at least one of a counter electrode and a reference electrode.

EMBODIMENT 25

The sensor according to any one of the preceding embodiments referring to a sensor, wherein the sensor further comprises at least one electrically insulating layer in between the membrane layer and the first electrically conductive material.

EMBODIMENT 26

The sensor according to any one of the preceding embodiments referring to a sensor, wherein the second electrically conductive material comprises at least one back electrode selected from the group consisting of a counter electrode and a reference electrode.

EMBODIMENT 27

The sensor according to the preceding embodiment, wherein the second electrically conductive material further comprises at least one electrically conductive lead for electrically contacting the at least one back electrode.

EMBODIMENT 28

The sensor according to any one of the preceding embodiments referring to a sensor, wherein the sensor further comprises at least one biocompatibility layer fully or partially surrounding the sensor.

EMBODIMENT 29

The sensor according to any one of the preceding embodiments referring to a sensor, wherein the sensor, besides the membrane, does not comprise any substrate, specifically no substrate extending over the full width of the sensor.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 5:
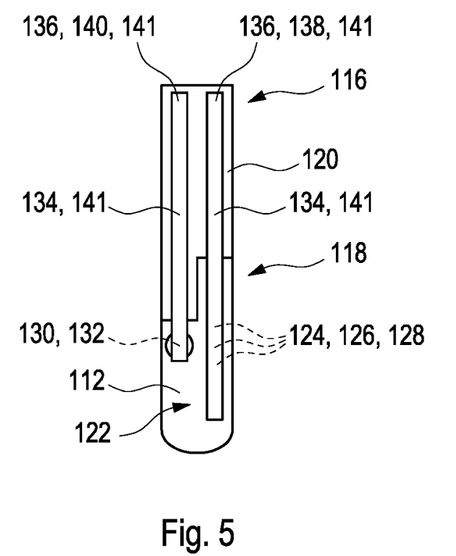
Figure 6:
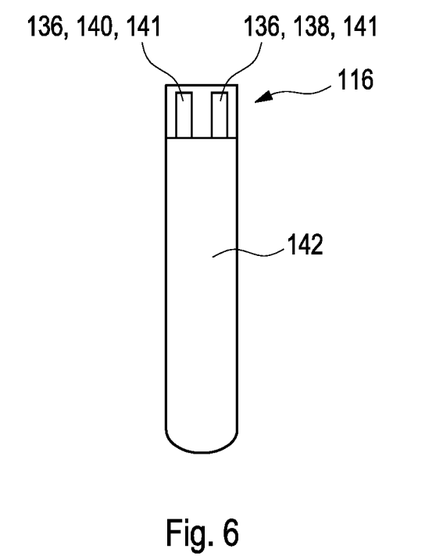
Figure 7:
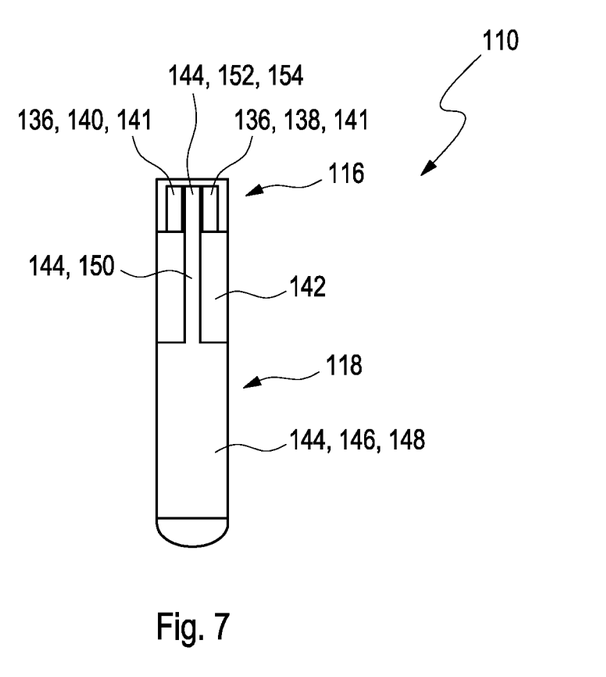
FIG. 7 shows the sensor for detecting the analyte in the body fluid manufactured by using the process steps and intermediate products of FIGS. 1 to 6.

In FIGS. 1 to 7, a method for manufacturing a sensor 110 for detecting an analyte in a body fluid is shown by possible process steps and intermediate products. The sensor 110 is shown in FIG. 7, whereas FIGS. 1 to 6 show various intermediate products. In the following, these figures will be explained jointly.

Figure 1:
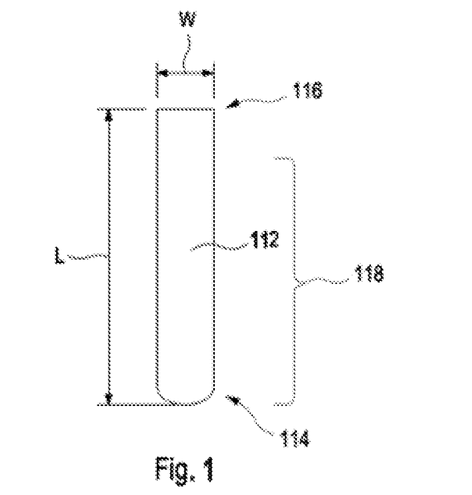
FIGS. 1 to 6 show intermediate products as exist during manufacturing of a sensor for detecting an analyte in a body fluid.

In a first method step, shown in FIG. 1, a membrane layer 112 is provided. The membrane layer 112, as an example, specifically may be permeable for the analyte to be detected. Thus, the membrane layer 112 may provide a selective barrier, allowing for the analyte to pass, whereas other molecules, such as molecules or compounds of a test material of the sensor 110, are retained within the sensor. As an example, the membrane layer may comprise one or more of a hydrogel or a polyurethane. The membrane layer 112 itself may function as a substrate for the sensor 110, replacing the commonly used flexible printed circuit boards, providing both the functionality of the semipermeable membrane as well as the functionality of mechanical stability. As an example, the membrane layer may have a length L of 2 mm to 30 mm, and a width W of 0.1 mm to 2 mm. The membrane layer 112, as an example, may have a thickness of 0.2 to 1.0 mm. The membrane layer 112 may be strip-shaped, as shown in FIG. 1, or may have another shape. The membrane layer 112, as an example, may have an insertable end 114 and a contact portion 116. The membrane layer 112 may provide an insertable portion 118 which, as an example, may have a constant width W. In the contact portion 116, the membrane layer 112 may also be widened as compared to the width W of the insertable portion 118.

The membrane layer 112, as outlined above, may be provided by various techniques. As an example, the membrane layer 112 may be provided in a reel-to-reel-process, wherein a plurality of membrane layers 112 are cut from a foil or endless tape. Alternatively, however, other techniques are feasible, such as casting or printing techniques for providing the membrane layer 112. For the membrane layer 112, as an example, at least one of a polyurethane, a polyacrylate or a hydrogel may be used. The membrane layer 112, as an example, may have a thickness of 1 µm to 150 µm.

Figure 2:
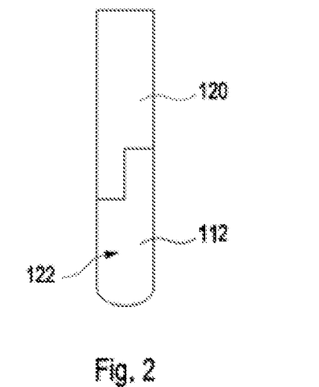

In a second and optional step, shown in FIG. 2, at least one electrically insulating layer 120 is deposited onto the membrane layer 112, such that one or more uncovered regions 122 remain free of the electrically insulating layer 120. (Note: the term "layer" is used herein interchangeably with "film" to avoid confusion between different insulating layers or materials discussed herein.) For this purpose, as an example, printing techniques may be used to deposit the electrically insulating layer 120 in a patterned fashion. As an example, an insulating resin may be used, such as an epoxy resin. The at least one electrically insulating layer 120, as an example, may have a thickness of <800 µm, preferred <500 µm, further preferred <300 µm or <200 µm, such as a thickness of 1 µm to 250 µm, specifically 5 µm to 50 µm. As an example, the electrically insulating layer 120 may have at least a thickness which is suitable to sustain the mechanical stress when implanted into the body tissue and, still, remains electrically insulating. The thickness, however, should be kept as low as possible, since obtaining homogeneous layers generally is more challenging for thick layers.

Figure 3:
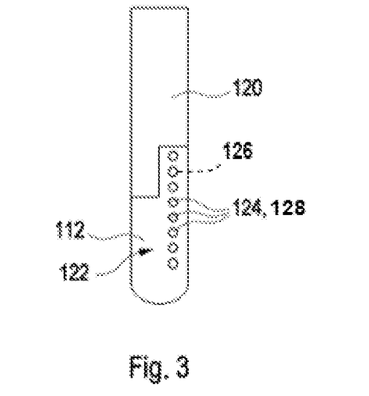

In a further process step, shown in FIG. 3, one or more working electrodes 124 are deposited onto the membrane layer 112, specifically onto one or more of the uncovered regions 122. The geometry of these working electrodes 124 may be chosen freely. Each working electrode, as an example, may comprise, firstly, a pad of one or more test chemicals 126, which is selectively sensitive to the analyte to be detected, e.g., for glucose. As an example, the test chemical 126 may be or may comprise glucose oxidase or other enzymes. Additionally, on a side facing away from the membrane layer 112, the working electrodes 124 may comprise electrically conductive working electrode pads 128, such as gold pads. These electrically conductive working electrode pads 128, however, may also be left out and may be combined with or replaced by electrically conductive leads, as will be explained in further detail below with respect to FIG. 5.

Figure 4:
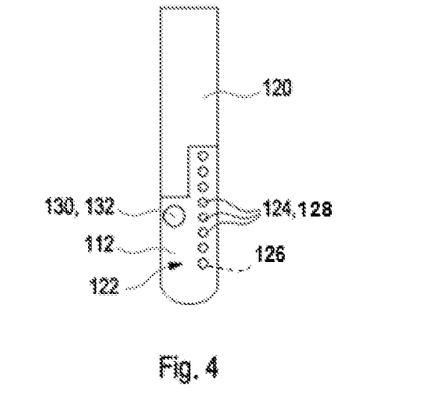

In a next and optional step, shown in FIG. 4, which may also be interchanged in order with the step of FIG. 3, one or more further electrodes 130 may optionally be deposited onto the membrane layer 112, specifically onto the uncovered region 122. The optional at least one further electrode 130 specifically may be or may comprise at least one reference electrode 132. Again, the geometry of the reference electrode 132 may be chosen according to the actual technical requirements of the sensor 110. The at least one reference electrode 132, as an example, may be or may comprise at least one redox material having known electrochemical properties which are not influenced by the presence or absence of the analyte to be detected. As an example, the reference electrode 132 may comprise Ag/AgCl. Again, as for the deposition of the working electrode 124, for depositing the at least one further electrode 130, printing techniques may be used, such as screen printing or other types of printing. Further, the at least one reference electrode 132 may be or may comprise at least one electrically conductive material. The at least one electrically conductive material, as an example, may be provided by an electrically conductive reference electrode pad, or the reference electrode 132, such as Ag/AgCl, itself may be electrically conductive.

In a further process step, shown in FIG. 5, one or more electrically conductive leads 134 may be provided, for electrically contacting the working electrodes 124 and, optionally, the at least one further electrode 130 such as the at least one reference electrode 132. As outlined above, electrically conductive electrode pads for the at least one working electrode 124 and, optionally also for the at least one further electrode 130, may also be provided in this step. These electrically conductive leads 134, as an example, may extend along a longitudinal axis of the membrane layer 112 and may extend from the contact portion 116 to the electrodes 124, 130 in the insertable portion 118. Therein, as shown, e.g., in FIG. 5, in case a plurality of working electrodes 124 are provided, all of these working electrodes 124 may be contacted by one and the same electrically conductive lead 134 or, alternatively, by separate electrically conductive leads 134. The step may also be used for providing contact pads 136 in the contact portion 116, which, by the electrically conductive leads 134, are connected to the respective electrodes 124, 130. Thus, as an example, the contact pads 136 may comprise at least one working electrode contact pad 138 and at least one reference electrode contact pad 140. By the electrically insulating layer 120, the contact pads 136 and the electrically conductive leads 134 are separated from the membrane layer 112, such that the analyte, preferably, may not get in contact with the electrically conductive leads 134 and the contact pads 136.

In the embodiment shown in FIGS. 1 to 7, the at least one electrically conductive lead 134 as well as the at least one contact pad 136 and, optionally, one or more electrode pads 128 of the electrodes 124, 130, may all be made of at least one first electrically conductive material 141, which, in the method step shown in FIG. 5 as well as further, optionally, also in the method steps shown in FIGS. 3 and 4, is deposited directly or indirectly onto the membrane layer 112. For depositing the at least one first electrically conductive material 141, various techniques are possible. As an example, the at least one first electrically conductive material 141 may be printed in a patterned fashion, such as by using screen printing.

In a subsequent process step, shown in FIG. 6, at least one electrically insulating material 142 (also referred to as "electrically insulating film") is deposited onto the intermediate product of FIG. 5, thereby covering at least the electrodes 124, 130 and the electrically conductive leads 134. Preferably, however, the covering by the electrically insulating material 142 is performed such that the contact pads 136, 138, 140 remain uncovered. For the electrically insulating material 142, again, as an example, electrically insulating resins may be used, such as one or more epoxy resins. The depositing of the at least one electrically insulating material 142, as an example, may be performed by printing techniques. Additionally or alternatively, however, continuous coating techniques may be used. The patterning of the electrically insulating material 142, thereby optionally leaving the contact pads 136 uncovered, may be performed simultaneously to the deposition of the electrically insulating material 142, by using a patterned deposition technique, or may be performed subsequently, e.g., by subsequently ablating the contact pads 136. The electrically insulating material 142 may form one or more electrically insulating layers. The electrically insulating material 142 will, later on, electrically separate the at least one working electrode 124 and, optionally, the at least one further electrode 130, which both are deposited on the membrane layer 112, from at least one further electrode on a side of the electrically insulating material 142 facing away from the membrane layer 112, thereby providing a sensor having electrodes on both sides.

In a further method step, shown in FIG. 7, at least one second electrically conductive material 144 is deposited on the electrically insulating material 142. The second electrically conductive material 144 may form or may comprise at least one back electrode 146 which, as an example, may be or may comprise a counter electrode 148. The counter electrode 148, as an example, may be or may comprise a metal electrode or, alternatively, may also be or may comprise a redox material, such as Ag/AgCl. As an example, the counter electrode 148 may be a large-area electrode, having an extension, e.g., over an area larger than the working electrodes 124.

The second electrically conductive material 144 may also comprise one or more electrically conductive leads 150 for contacting the at least one back electrode 146. The second electrically conductive material 144 may also comprise one or more contact pads 152, such as one or more back electrode contact pads 154, which, as an example, are in electrical contact with the electrically conductive lead 150, for electrically contacting the back electrode 146. Thus, with the contact pads 136 of the first electrically conductive material 141 remaining free of the electrically insulating material 142, contact pads 136 are provided for contacting the front electrodes, comprising the at least one working electrode 124 and optionally the at least one further electrode 130, and at least one contact pad 152 of the second electrically conductive material 144 is provided for electrically contacting the at least one back electrode 146.

The process for manufacturing the sensor 110 may comprise additional method steps, and the sensor 110 may comprise additional elements not shown in FIGS. 1 to 7. Thus, as an example, the sensor 110, in a further step, may fully or partially be coated with one or more additional materials, such as one or more biocompatibility layers, for, e.g., covering the back electrode 146. For the at least one biocompatibility layer, as an example, again, membrane materials may be used, which are permeable for the analyte and/or other materials which increase biocompatibility of the sensor 110.

Further, one or more singulation steps may be used, e.g., in case a plurality of sensors 110 is manufactured in a combined fashion, such as one or more cutting steps.

It shall further be noted that one or more of the process steps shown in the Figures may also fully or partially be combined. Thus, as an example, the process steps shown in FIG. 5 may also be combined with one or more of the process steps of FIGS. 4 and/or 3. As an example, the at least one further electrode 130 may simultaneously be generated with the electrically conductive leads 134. Thus, the step of depositing the at least one first electrically conductive material 141 may be or may comprise a single step or may comprise a plurality of process steps, e.g., printing steps. Further, one or more of the process steps shown in the Figures may also have a plurality of substeps. Thus, as an example, the depositing of the at least one first electrically conductive material 141 and/or the depositing of the second electrically conductive material 144 each, independently, may be a single-step process or a multiple-step process.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 sensor
112 membrane layer
114 insertable end
116 contact portion
118 insertable portion
120 electrically insulating layer
122 uncovered region
124 working electrode
126 test chemical
128 electrically conductive working electrode pad
130 further electrode
132 reference electrode
134 electrically conductive lead
136 contact pad
138 working electrode contact pad
140 reference electrode contact pad
141 first electrically conductive material
142 electrically insulating material
144 second electrically conductive material
146 back electrode
148 counter electrode
150 electrically conductive lead
152 contact pad
154 back electrode contact pad

What is claimed is:

1. A method for manufacturing a sensor for detecting an analyte in a body fluid, the method comprising steps of:
   providing a membrane layer;
   forming at least one electrode pad of a working electrode by depositing at least one chemical reagent onto a region of the membrane layer and depositing a first electrically conductive material onto the at least one chemical reagent;
   forming an electrically conductive lead on the at least one electrode pad of the working electrode;
   forming at least one electrode pad of a further electrode, wherein the further electrode is chosen from the group consisting of a counter electrode and a reference electrode, by depositing an electrically conductive material directly onto the membrane layer;
   forming an electrically conductive lead on the at least one electrode pad of the further electrode; and
   depositing an electrically insulating material onto the membrane layer, the at least one electrode pad of the working electrode, the electrically conductive lead of the working electrode, the at least one electrode pad of the further electrode and the electrically conductive lead of the further electrode to form the sensor.

2. The method according to claim 1, wherein the providing the membrane layer comprises providing a selective barrier that is permeable for the analyte.

3. The method according to claim 1, further comprising depositing a second electrically conductive material on the electrically insulating material to form at least one electrode pad for a back electrode selected from the group consisting of a counter electrode and a reference electrode.

4. A method for manufacturing a sensor for detecting an analyte in a body fluid, the method comprising steps of:
   providing a membrane layer;
   depositing a first electrically conductive material onto the membrane layer;
   depositing an electrically insulating material onto the membrane layer and the first electrically conductive material;
   depositing a second electrically conductive material onto the electrically insulating material; and
   wherein the depositing of the first electrically conductive material further comprises forming an electrically conductive lead for electrically contacting an electrode and the method further comprises, before forming the electrically conductive lead for electrically contacting the electrode, depositing an electrically insulating layer onto the membrane layer, wherein the electrically insulating layer is disposed between the conductive lead and the membrane layer.

5. The method according to claim 4, wherein the depositing of the second electrically conductive material comprises forming at least one electrode pad for a back electrode selected from the group consisting of a counter electrode and a reference electrode.

6. A method for manufacturing a sensor for detecting an analyte in a body fluid, the method comprising steps of:
   providing a membrane layer;
   depositing a first electrically conductive material onto the membrane layer;
   depositing an electrically insulating material onto the membrane layer and the first electrically conductive material;
   depositing a second electrically conductive material onto the electrically insulating material; and
   wherein the depositing of the second electrically conductive material comprises forming at least one electrode pad for a back electrode selected from the group consisting of a counter electrode and a reference electrode, and forming an electrically conductive lead for electrically contacting the back electrode.

* * * * *